United States Patent [19]

Bollé et al.

[11] Patent Number: 4,934,807
[45] Date of Patent: Jun. 19, 1990

[54] SUNGLASSES HAVING DETACHABLE ABSORBER STRIP

[75] Inventors: Maurice Bollé, Oyonnax, France; Dean Bassett, Lakewood, Colo.

[73] Assignee: Establissements Bolle' S.N.C., France

[21] Appl. No.: 161,852

[22] Filed: Feb. 29, 1988

[51] Int. Cl.⁵ .................... G02C 11/08; G02C 5/20
[52] U.S. Cl. ......................... 351/62; 351/118; 351/44
[58] Field of Search .............. 351/118, 44, 86, 62, 351/47, 158, 436; 2/437

[56] References Cited

U.S. PATENT DOCUMENTS

| | | |
|---|---|---|
| 2,444,498 | 7/1948 | Cochran . |
| 2,472,731 | 6/1949 | Splaine . |
| 2,582,345 | 1/1952 | Moeller . |
| 2,700,765 | 2/1955 | Hoffmaster ................ 351/44 |
| 3,133,982 | 5/1964 | Janz ........................ 351/62 |
| 3,233,249 | 2/1966 | Baratelli et al. . |
| 3,233,250 | 2/1966 | Jonassen . |
| 3,368,221 | 2/1968 | Anderson ................... 2/437 |
| 3,531,189 | 9/1970 | Petito ...................... 351/47 |
| 3,689,136 | 9/1972 | Atamian .................... 351/44 |
| 4,515,448 | 5/1985 | Tackles .................... 351/41 |
| 4,571,748 | 2/1986 | Carroll et al. ............. 2/436 |
| 4,674,851 | 6/1987 | Jannard .................... 351/47 |

FOREIGN PATENT DOCUMENTS 303716  1/1929  United Kingdom ............... 351/118

*Primary Examiner*—Rodney B. Bovernick
*Attorney, Agent, or Firm*—Rosen, Dainow & Jacobs

[57] ABSTRACT

Sunglasses have a removable and replaceable transparent convex pane curved both horizontally and vertically. Moisture absorbing means comprising a foam absorber strip is removably attached to the frame. Adjustable, interchangeable temple members are provided for optimal fit and comfort.

8 Claims, 3 Drawing Sheets

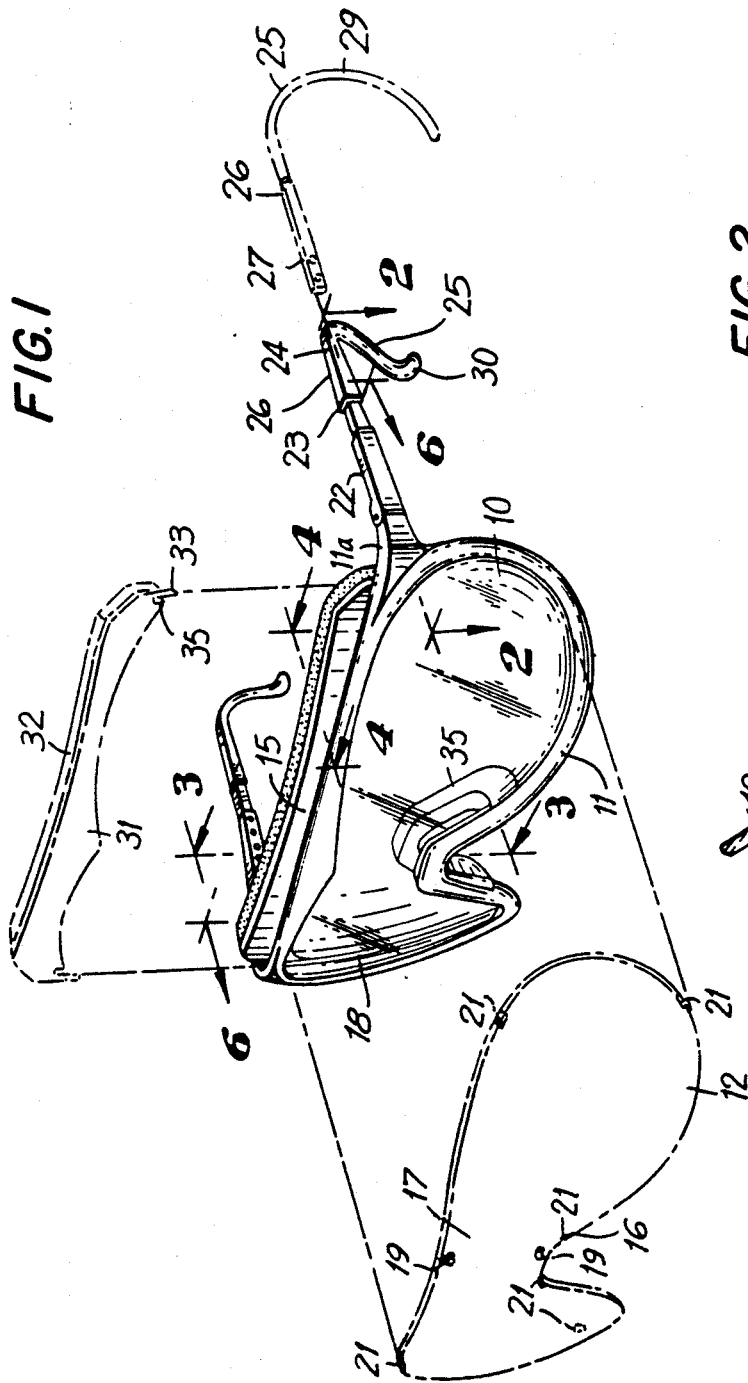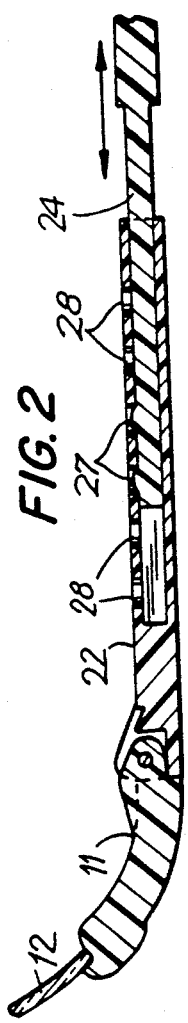

FIG. 3
FIG. 4
FIG. 5
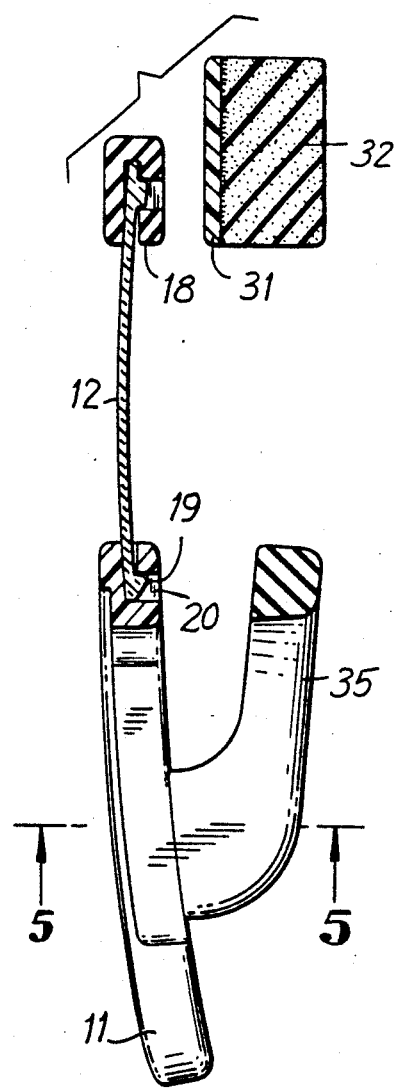
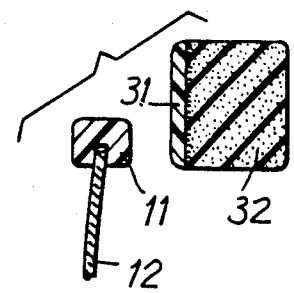
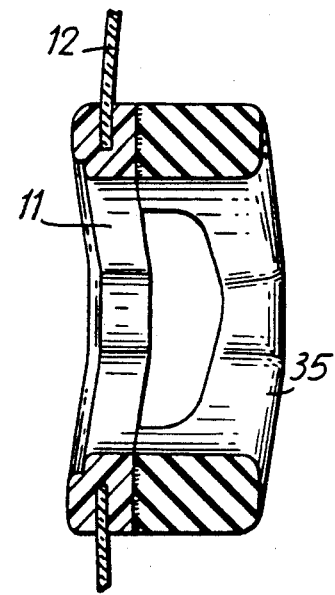

FIG. 6
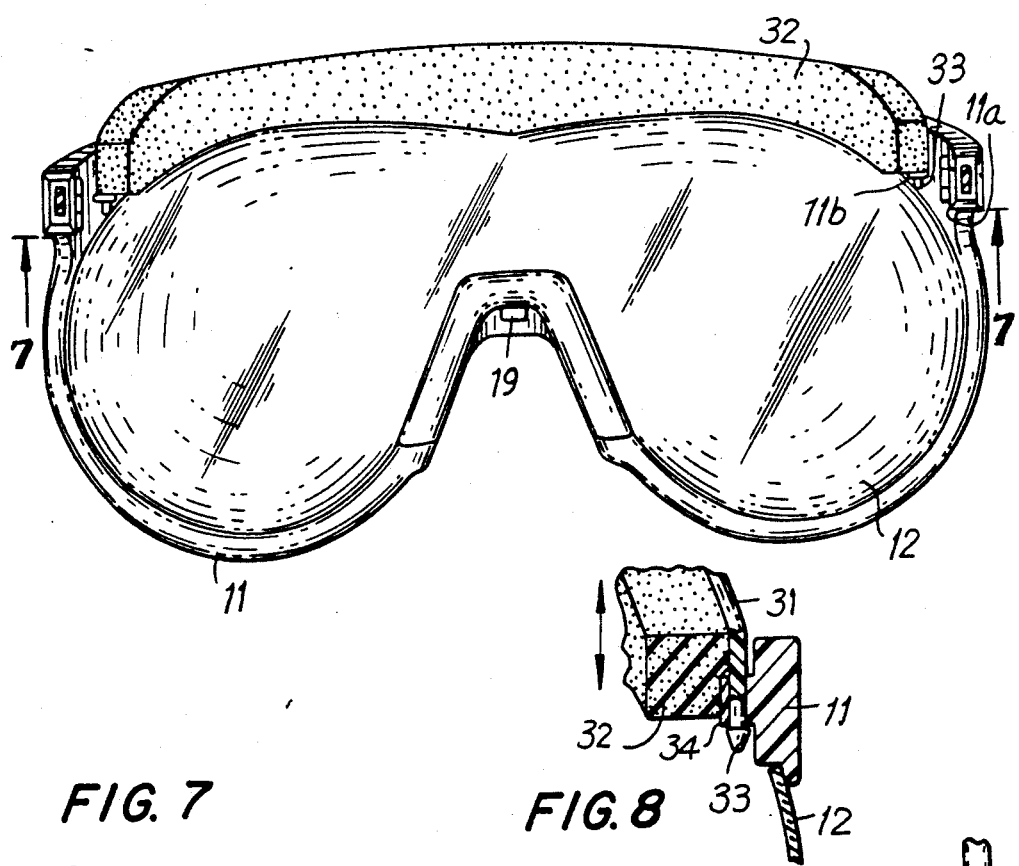
FIG. 7
FIG. 8
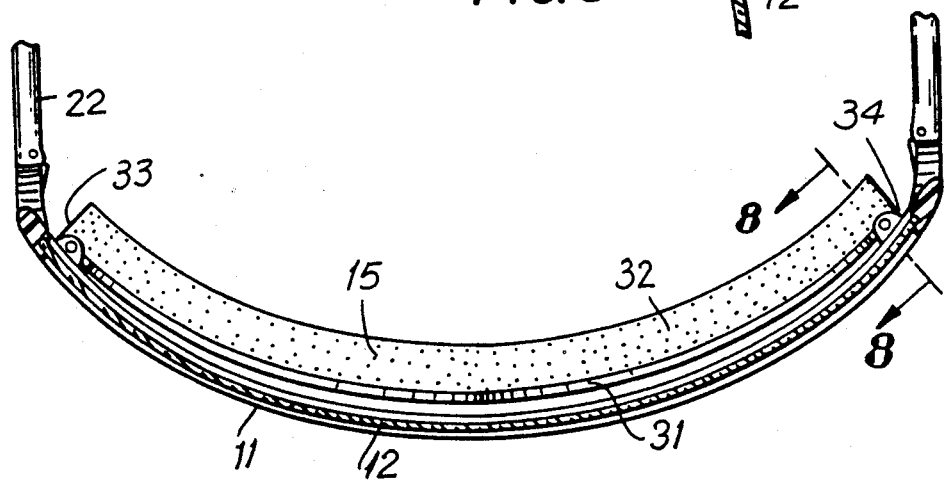

SUNGLASSES HAVING DETACHABLE ABSORBER STRIP

BACKGROUND OF THE INVENTION

This invention relates to protective eyewear and specifically to sunglasses.

There is a need for lightweight, comfortable, securely fitting sunglasses which not only protect the wearer's eyes from sunlight, glare, wind and from moisture on the pane but which are also attractive in appearance. There is also a need for sunglasses which can be assembled and adjusted by the wearer for better fit and comfort, and so as to permit wear under variable light and weather conditions.

Accordingly, it is an object of this invention to provide improved sunglasses which more completely protect the wearer's eyes from sunlight glare, wind and particles and which at the same time permit unobstructed front and peripheral vision.

It is a further object of this invention to provide sunglasses wherein the pane is readily removable and replaceable with other panes of varying color and intensity so that the sunglasses may be adapted to suit changing light and weather conditions.

Another object of this invention is the provision of sunglasses which have moisture absorbing means so as to permit lens ventilation and protect the wearer from moisture on the pane.

A final object of this invention is the provision of sunglasses having removable and replaceable components which are easy to assemble and adjust for optimal fit and comfort.

SUMMARY OF THE INVENTION

It will be seen that the sunglasses of this invention meet the above requirements of visibility and eye protection and feature additional advantages in construction and ease of assembly. The improved sunglasses of this invention comprise a single, transparent, convex pane curved rearwardly to conform substantially to the general curvature of a wearer's face in the eye region, so as to extend continuously across the wearer's right, left and side fields of vision. The pane of the sunglasses, in addition to being curved horizontally, is also curved vertically. The lower portion of the sunglasses thus hugs the upper cheek area over an extended range. Aside from improving the wind resistance of the sunglasses, the vertical curvature of the pane protects the wearer's eyes from particles such as pebbles which are dislodged and thrown by moving objects, for example bicycles. This wrap-around design of the pane results in unobstructed front and peripheral vision and extra protection from the sun and wind. As will be seen, the frame is also shaped in a rearward and downward curving convex configuration to match the convex curve of the pane and to facilitate pane removal and replacement.

Attached to the frame is a foam absorber strip which absorbs moisture from the wearer's brow, preventing moisture from penetrating the interior of the glasses and interfering with the wearer's vision.

As will be explained, both the foam absorber strip and the pane are independently removably attached to the frame, so as to permit the wearer to selectively remove and replace either the pane or the foam absorber strip. Additionally, temple members are provided which may be adjusted by the wearer to bring the pane closer to the face and to insure a better fit of the glasses. Alternately, temple members having different shapes or sizes may be selected and inserted in the arms. It is envisioned that a supply of interchangeable panes in a variety of colors and intensities to suit light and weather conditions and a variety of temple members and foam absorbers in different sizes, shapes and colors to fit a variety of head contours, will be available for selection and assembly by the wearer to assure optimal fit and comfort.

It is preferred that the pane have vertical as well as horizontal curvature. This rearward and downward convex curvature of the pane maximizes continuous contact of the sunglasses with the face, from the foam absorber strip along the top of the frame to the cheek-contacting lower peripheral portions of the sunglasses, so as to increase wind resistance and protect against particles penetrating to the eyes of the wearer.

With these and other advantages in view, the invention will be more fully understood with reference to the following description and drawings wherein:

DRAWING DESCRIPTION

FIG. 1 is a perspective view of one embodiment of the assembled sunglasses of the present invention, with removable component parts shown in phantom lines;

FIG. 2 is a cross-sectional view taken along lines 2—2 of FIG. 1;

FIG. 3 is a cross-sectional view taken along lines 3—3 of FIG. 1;

FIG. 4 is a cross-sectional view taken along lines 4—4 of FIG. 1;

FIG. 5 is a cross-sectional view taken along lines 5—5 of FIG. 3;

FIG. 6 is a rear elevation view of the embodiment of the sunglasses of this invention;

FIG. 7 is a bottom plan view taken along lines 7—7 of FIG. 6.

FIG. 8 is a cross-sectional view taken along lines 8—8 of FIG. 7.

DETAILED DESCRIPTION

In the drawings, identical reference numbers are used to designate similar parts of the structure. As will be described, the sunglasses of the present invention are symmetrical about a vertical center plane passing through the bridge. Therefore, only one side of the structure will be described in detail.

The protective eyewear of the present invention, as for example sunglasses shown generally as 10 in FIG. 1, includes a light weight, nylon or plastic frame 11, a single, transparent, convex pane 12 curved rearwardly to conform substantially to the general curvature of a wearer's face in the eye region, arms 23, temple members 24, and foam absorber strip 15. Shown in phantom lines in FIG. 1 are the various components of the sunglasses of this invention, as they would appear disassembled.

The single, transparent convex pane 12 of the present invention is curved rearwardly to conform substantially to the front and side configuration of a wearer's face in the eye region, i.e. the pane curves in a uniform convex fashion so as to wrap around the wearer's eyes and extend rearwardly along the sides of the face, so as to extend continuously across the wearer's right, left and side fields of vision. The pane 12 of the sunglasses, in addition to being curved horizontally, is also curved vertically. The lower portion of the sunglasses thus hugs the lower eye region of the face over an extended range.

The pane 12 has a nose recess 16 in the central portion of the lower edge thereof, intermediate its ends, said nose recess 16 curved in a generally triangular shape to fit the nose. A bridge area 17 is located above the nose recess 16, midway between the ends of the pane. Symmetrical, mirror-image right and left sides of the pane 12 are thus located at opposite sides of an imaginary vertical plane bisecting the bridge area 17 and are integrally connected by said bridge area 17.

A convex frame 11 extends along and bounds the outer perimeter of the pane 12. The frame 11 has a rearward and downward curving convex configuration to match the convex curve of the pane, so as to wrap around the wearer's eyes and extend rearwardly along the sides of the face.

As indicated in FIGS. 1 and 3, pane 12 is removably secured in frame 11. The frame 11 has a longitudinal pane retaining slot 18 extending along its inner periphery. The slot 18 is adapted to receive and support the periphery of pane 12. The flexible pane 12 may be inserted in the frame 11 slot opening by deflecting the upper and lower peripheral portions of the frame 11 sufficiently to permit the pane 12 to be pressed into position. The pane 12 is then snapped into place in the frame 11 and firmly retained in the pane retaining slot 18.

To facilitate locking engagement of the pane 12 in the frame 11, projections 19 are provided on the upper and lower peripheral portions of the bridge area 17 of the pane for engagement with complementary openings 20 in the frame. The diameter of the projections 19 is preferably greater than the width of the openings 20 so that a snap action results when projections 19 engage with or are released from openings 20. The pane 12 is locked into the frame 11 when projections 19 are pressed through and engage with openings 20. The pane 12 is released when projections 19 and openings 20 are pulled apart from each other. Any number of projections 19 and openings 20 may be provided; however, in the preferred embodiment only two sets of projections 19 and openings 20 are provided, at the upper and lower peripheral portions of the bridge area 17.

In the preferred embodiment, a variety of panes in a choice of colors and intensities is available for selection by the wearer to suit changing light and weather conditions. The selected pane 12 may be quickly inserted in the frame by deflecting the frame 11 slightly to permit the pane 12 to be installed in the slot 18 in the frame 11 and simply snapping the complementary projections 19 and openings 20 together. Similarly, to remove the pane 12, the frame 11 is deflected slightly and pane projections 19 pulled out of frame openings 20.

In a preferred embodiment, the inner marginal edges of the pane 12 are notched at regular intervals. Such notches 21, indicated in the exploded view of the pane in FIG. 1, facilitate engagement of the pane 12 in the frame 11.

Pivotally attached to opposite upper end extents 11a of the frame 11 are hollow arms 22 which project horizontally towards the wearer's ears. Each arm 22 is between 1 and 2 inches long and is adapted to engage with a temple member 24 to form earpiece 23.

Each temple member 24 comprises a curved portion 25 adapted to engage the wearer's ears and a straight portion 26 of reduced diameter. As indicated in FIG. 2, the inner surfaces of the straight portions 26 of the temple members 24 have laterally projecting dimples 27 that enter and releaseably engage with a respective cavity 28 on the inner surface of the arm 22 when assembled. A plurality of cavities 28 may be provided on the arms 22. The sunglasses of this invention may be adjusted to fit the wearer's face by pressing the temple members 24 so as to cause the dimples 27 to move in or out of the cavities 28 in the arms 22, thus lengthening or shortening the length of the earpieces 23. Through the medium of this adjustable feature, namely on the arms 22, it is possible not only for the wearer to adjust the sunglasses to fit his face, but to remove and replace the temple members 24 on the frame 11 with alternates available in a variety of shapes and sizes. For instance, cable 29 and straight 30 temple members may be provided, as indicated in FIG. 1.

An elongated foam absorber strip 15 comprising a flexible plastic band 31 having an elongated foam strip 32 adhesively mounted thereon contacts the wearer's brow and absorbs moisture therefrom. As indicated in FIGS. 6 and 7, the foam absorber strip 15 extends transversely, adjacent the top and inner peripheral portions of the frame 11. The foam absorber strip 15 is independently and removably attached to the frame 11 and held in a spaced relation therefrom via downwardly extending pin members 33, located at opposite ends of band 31. Pin members 33 are adapted to enter and releaseably engage with pin housing members 34 provided at opposite ends of the upper interior surface of the frame 11 proximate the attachment of the arms 22. As indicated in phantom lines in FIG. 1, upward notches 35 are provided on the band 31 of the foam absorber strip 15 proximate said downwardly extending pin members 33 to accommodate the pin housing members 34.

A substantially U-shaped nose piece 35 of semi-rigid plastic or similar resilient material is attached at its lateral peripheral portions to the interior surface of the upwardly curved portions of the frame 11 defining the nose recess 16 and projects upward and outwardly therefrom. The nose piece 35, which is adapted to contact the wearer's nose, rests the glasses comfortably on the wearer's nose, and aids in retaining the glasses in position by resisting the tendency of the glasses to slide from the nose when perspiration is present.

It will be understood that other protective eyewear may be made without departing from the spirit of this invention or the scope of the appended claims.

I claim:

1. Protective eyewear comprising the combination of:
   (a) a single, transparent eye protector;
   (b) a frame for holding said eye protector:
   (c) moisture absorbing means removably attached to said frame, comprising a flexible plastic band having an elongated moisture absorber strip mounted thereon, said band having downwardly extending pin members at opposite ends thereof adapted to enter and releaseably engage with pin housing members provided at opposite ends of the upper interior surface of the frame, said moisture absorbing strip held in spaced relation to said frame when said pin members are engaged in said pin housing members.

2. Protective eyewear comprising the combination of:
   (a) a single, transparent eye protector;
   (b) a frame for holding said eye protector;
   (c) arms for engaging a wearer's ears attached to said frame;

(d) an elongated foam absorber strip for removable attachment to said frame, comprising a flexible plastic band having an elongated foam strip adhesively mounted thereon, said band having downwardly extending pin members at opposite ends thereof adapted to enter and releaseably engage with pin housing members provided at opposite ends of the upper interior surface of the frame proximate the attachment of said arms, upward notches being provided on said band proximate said downwardly extending pin members, said foam absorber strip held in spaced relation to said frame when said pin members are engaged in said pin housing members.

3. Protective eyewear comprising the combination of:
(a) a single, transparent pane;
(b) a frame for holding said pane;
(c) means for releaseably retaining said pane in said frame, said means comprising the combination of a slot extending along the periphery of the frame, said slot adapted to receive and support the periphery of the pane, and projections on said pane and openings in said frame, said projections being engageable with said openings to secure the frame and pane together when said pane is inserted in said slot in the frame, said frame being of sufficiently resilient material to permit displacement over said projections in said pane for disengaging said pane;
(d) a foam absorber strip for removable attachment to said frame, comprising a flexible plastic band having an elongated foam strip mounted thereon, said band having downwardly extending pin members at opposite ends thereof adapted to enter and releaseably engage with pin housing members provided at opposite ends of the upper interior surface of the frame, said foam absorber strip held in spaced relation to said frame when said pin members are engaged in said pin housing members.

4. Protective eyewear comprising the combination of:
(a) a single, transparent pane;
(b) a frame for holding said pane, said frame having a longitudinal slot extending along the inner periphery thereof, said slot adapted to receive and support the periphery of the pane;
(c) means for releaseably retaining said pane in said frame comprising projections carried by said pane and complementary openings provided in said frame, said projections being engageable with said openings to secure the frame and pane together, said frame being of sufficiently resilient material to permit displacement over said projections in said pane for disengaging said pane;
(d) an elongated foam absorber strip for removable attachment to said frame, comprising a flexible plastic band having an elongated foam strip adhesively mounted thereon, said band having downwardly extending pin members at opposite ends thereof adapted to enter and releaseably engage with pin housing members provided at opposite ends of the upper interior surface of the frame proximate the attachment of said arms, upward notches being provided on said band proximate said downwardly extending pin members, said foam absorber strip held in spaced relation to said frame when said pin members are engaged in said pin housing members.

5. Protective eyewear comprising the combination of:
(a) a transparent convex pane curved rearwardly to conform the eye region, so as to extend continuously across the wearer's right, left and side fields of vision, and curved downwardly so as to hug the wearer's cheek area over an extended range, said pane having a nose recess, a bridge above said nose recess and symmetrical right and left sides integrally connected by said bridge area;
(b) a convex frame extending along and bounding the perimeter of the pane;
(c) means for releaseably retaining said pane in said frame, said means comprising the combination of a slot extending along the periphery of said frame, said slot adapted to receive and support the periphery of the pane and projections on said pane and openings in said frame, said projections being engageable with said openings to secure the frame and pane together when said pane is inserted in said slot in the frame;
(d) hollow arms attached to opposite upper end extents of said frame, said arms adapted to project horizontally towards the wearer's ears, said arms having a length between 1 and 2 inches and a plurality of cavities on the inner surface thereof;
(e) a temple member for removable attachment to each of said arms, comprising a curved portion adapted to engage the wearer's ears and a straight portion of reduced diameter, said straight portion having a plurality of dimples along its inner surface adapted to fit into and releaseably engage with the cavities in the inner surfaces of the arms;
(f) an elongated foam absorber strip for removable attachment to said frame, comprising a flexible plastic band having an elongated foam strip mounted thereon, said band having downwardly extending pin members at opposite ends thereof adapted to enter and releaseably engage with pin housing members provided at opposite ends of the upper interior surface of the frame, said foam absorber strip held in spaced relation to said frame when said pin members are engaged in said pin housing members.

6. Protective eyewear comprising the combination of:
(a) a transparent convex pane curved rearwardly to conform substantially to the general curvature of a wearer's face in the eye region, so as to extend continuously across the wearer's right, left and side fields of vision, and curved downwardly to hug the wearer's lower eye region over an extended range, said pane having a nose recess, a bridge above said nose recess and symmetrical right and left sides integrally connected by said bridge area;
(b) a convex frame extending along and bounding the perimeter of said pane;
(c) means for releaseably retaining said pane in said frame, said means comprising the combination of a slot extending along the periphery of the frame, said slot adapted to receive and support the periphery of the pane and projections on said pane and openings in said frame, said projections being engageable with said openings to secure the frame and pane together when said pane is inserted in said slot in the frame;
(d) hollow arms attached to opposite upper end extents of said frame, said arms adapted to project horizontally towards the wearer's ears, said arms having a length between 1 and 2 inches and a plurality of cavities on the inner surface thereof;

(e) a temple member for removable attachment to each of said arms, comprising a curved portion adapted to engage the wearer's ears and a straight portion of reduced diameter, said straight portion having a plurality of dimples along its inner surface adapted to fit into and releaseably engage with the cavities in the inner surfaces of the arms;

(f) an elongated foam absorber strip for removable attachment to said frame, comprising a flexible plastic band having an elongated foam strip adhesively mounted thereon, said band having downwardly extending pin members at opposite ends thereof adapted to enter and releaseably engage with pin housing members provided at opposite ends of the upper interior surface of the frame proximate the attachment of said arms, upward notches being provided on said band proximate said downwardly extending pin members, said foam absorber strip held in spaced relation to said frame when said pin members are engaged in said pin housing members.

7. Protective eyewear comprising the combination of:
(a) a single, transparent, convex pane curved rearwardly face in the eye region, so as to extend continuously across the wearer's right, left and side fields of vision, and curved downwardly to hug the wearer's cheek area over an extended range, said pane having a nose recess in the central portion of the lower edge thereof, a bridge above said nose recess and symmetrical right and left sides integrally connected by said bridge area;
(b) a convex frame extending along and bounding the perimeter of the pane, said frame having a longitudinal slot extending along the inner periphery thereof, said slot adapted to receive and support the periphery of the pane;
(c) means for releaseably retaining said pane in said frame comprising projections carried by said pane and complementary openings provided in said frame, said projections being engageable with said openings to secure the frame and pane together, said frame being of sufficiently resilient material to permit displacement over said projections in said pane for disengaging said pane;
(d) hollow arms attached to opposite upper end extents of said frame, said arms adapted to project horizontally towards the wearer's ears, said arms having a length between 1 and 2 inches and a plurality of cavities on the inner surface thereof;
(e) a temple member for removable attachment to each of said arms, comprising a curved portion adapted to engage the wearer's ears and a straight portion of reduced diameter, said straight portion having a plurality of dimples along its inner surface adapted to fit into and releaseably engage with the cavities in the inner surfaces of the arms;
(f) an elongated foam absorber strip for removable attachment to said frame, comprising a flexible plastic band having an elongated foam strip adhesively mounted thereon, said band having downwardly extending pin members at opposite ends thereof adapted to enter and releaseably engage with pin housing members provided at opposite ends of the upper interior surface of the frame proximate the attachment of the arms, upward notches being provided on said band proximate said downwardly extending pin members, said foam absorber strip held in spaced relation to said frame when said pin members are engaged in said pin housing members.

8. The combination of claim 7 wherein said eyewear comprises sunglasses.

* * * * *

UNITED STATES PATENT AND TRADEMARK OFFICE
CERTIFICATE OF CORRECTION

PATENT NO.  : 4,934,807

DATED       : June 19, 1990

INVENTOR(S) : Maurice Bolle et al.

It is certified that error appears in the above-identified patent and that said Letters Patent is hereby corrected as shown below:

Column 4, line 10, after "namely" insert --dimples 27 on the temple members 24 and complementary cavities 28--.

Coulmn 6, line 2, after "conform" insert --substantially to the general curvature of a wearer's face in--.

Column 7, lines 24-25, after "rearwardly" insert --to conform substantially to the general curvature of a wearer's--.

Signed and Sealed this

Thirteenth Day of August, 1991

*Attest:*

HARRY F. MANBECK, JR.

*Attesting Officer*     Commissioner of Patents and Trademarks